United States Patent [19]

Gall et al.

[11] Patent Number: 4,871,094

[45] Date of Patent: Oct. 3, 1989

[54] MEANS AND METHOD FOR DISPENSING SUBSTANCES

[75] Inventors: Russell A. Gall, Cupertino, Calif.; Don A. Clements, Arlington; Michael J. Kent, Forth Worth, both of Tex.

[73] Assignee: Alcon Laboratories, Inc., Fort Worth, Tex.

[21] Appl. No.: 188,355

[22] Filed: Apr. 29, 1988

Related U.S. Application Data

[63] Continuation-in-part of Ser. No. 948,207, Dec. 31, 1986, abandoned.

[51] Int. Cl.$^4$ .................................. A61M 35/00
[52] U.S. Cl. ........................... 222/386; 222/79; 222/541; 604/59; 604/298
[58] Field of Search ................. 222/79, 309, 325–327, 222/340, 391, 541, 386; 604/59–64, 207–211, 223, 200, 294, 295, 298, 299; 600/7, 8

[56] References Cited

U.S. PATENT DOCUMENTS

| | | | |
|---|---|---|---|
| 1,393,720 | 10/1921 | Lomas et al. | 604/210 |
| 1,546,491 | 7/1925 | Kasmauskas | 604/206 |
| 2,059,966 | 11/1936 | Kaufman et al. | 222/327 |
| 2,368,432 | 1/1945 | Smith | 604/235 |
| 2,572,155 | 10/1951 | Hoyt | 222/327 |
| 2,647,512 | 8/1953 | Johnson | 604/64 |
| 3,744,493 | 7/1973 | Booher | 604/62 |
| 3,934,585 | 1/1976 | Maurice | 604/298 |
| 3,972,683 | 8/1976 | Lape | 222/249 |
| 4,017,007 | 4/1977 | Riccio | 222/325 |
| 4,257,267 | 3/1981 | Parsons | 222/309 |
| 4,475,905 | 10/1984 | Himmelstrup | 604/208 |
| 4,496,344 | 1/1985 | Kamstra | 604/90 |
| 4,583,974 | 4/1986 | Kokernak | 604/211 |
| 4,623,337 | 11/1986 | Maurice | 604/298 |

FOREIGN PATENT DOCUMENTS

| | | | |
|---|---|---|---|
| 1223495 | 8/1956 | Fed. Rep. of Germany | 604/62 |
| 1156298 | 5/1958 | France | 604/209 |
| 0252587 | 6/1926 | United Kingdom | 604/60 |

*Primary Examiner*—Andres Kashnikow
*Assistant Examiner*—Karen B. Merritt
*Attorney, Agent, or Firm*—Zarley, McKee, Thomte, Voorhees & Sease

[57] ABSTRACT

A dispenser for substances including solids, liquids, semi-solids, and gels including a forward member having a bore extending between its front and back opposite ends. The front end of the forward member consists of an application orifice. A rearward member is translateably movable with respect to the forward member and includes a plunger which is extendable through the back end of the forward member into the bore of the forward member. The plunger is slidable in the bore in response to movement of the forward section with respect to the rearward section. The substance, having been inserted into the bore, is then expelled from the application orifice in a precise and easily maneuverable manner. The dispensing means can be used with substances which are pre-packaged in capillary-type containers. The plunger can have different diametered sections which allow expulsion of the substance and then allow expulsion of the capillary-type container. Additionally, the capillary-type containers can hold a plurality of doses of the substance for multiple measured applications. Guide structure can be incorporated between the forward and rearward sections to control movement of the forward and rearward sections during application of the substance. A disposable tip can also contain a pre-loaded dosage and be detachably mountable to the forward member.

21 Claims, 6 Drawing Sheets

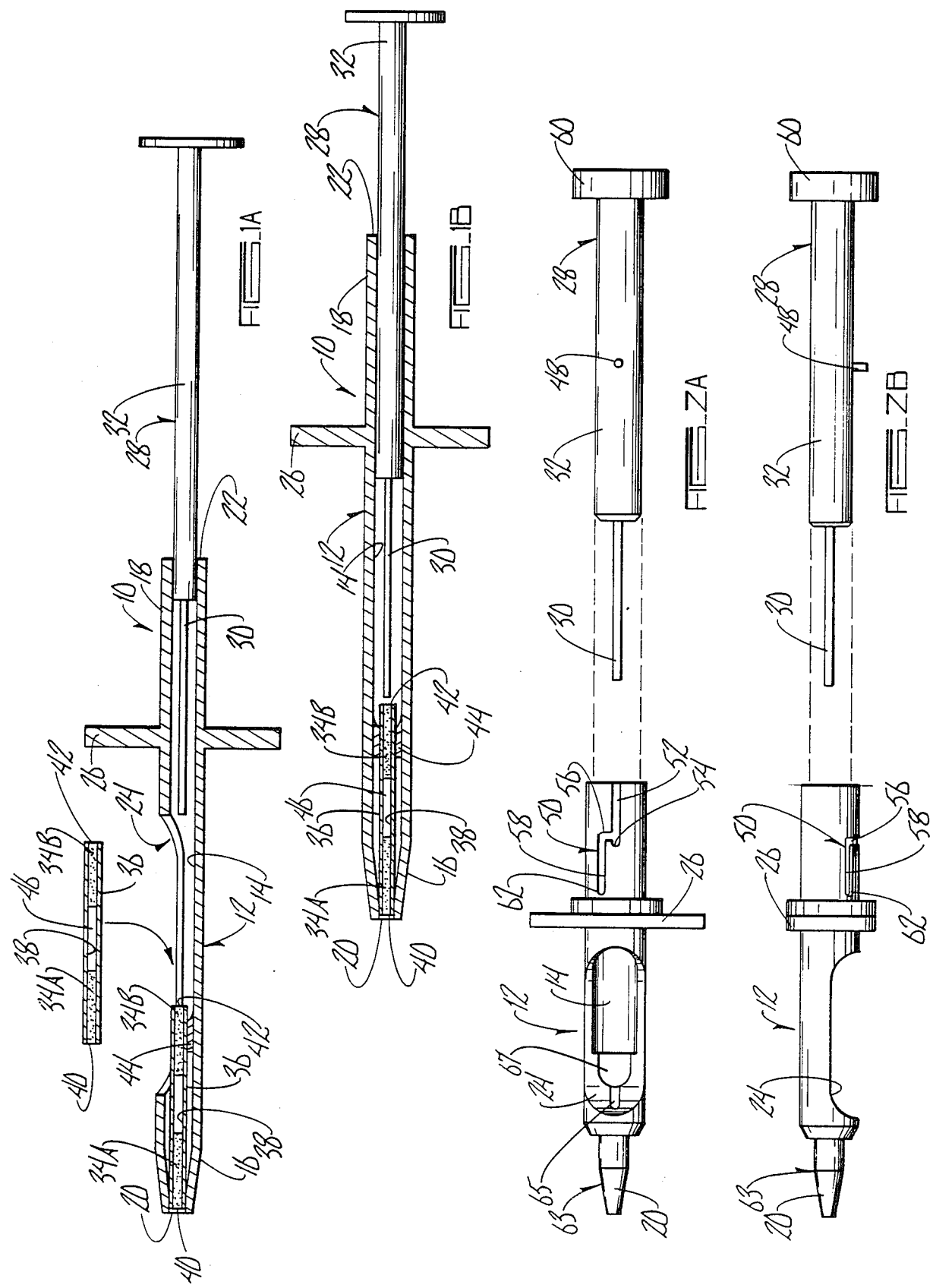

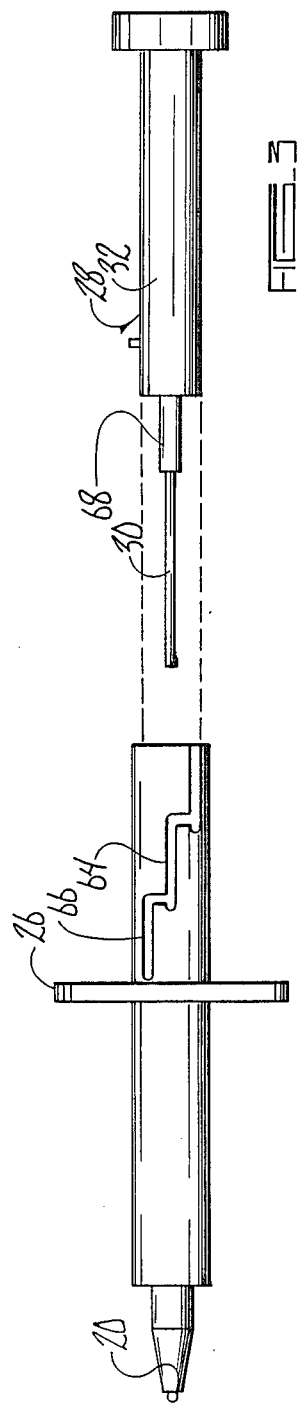

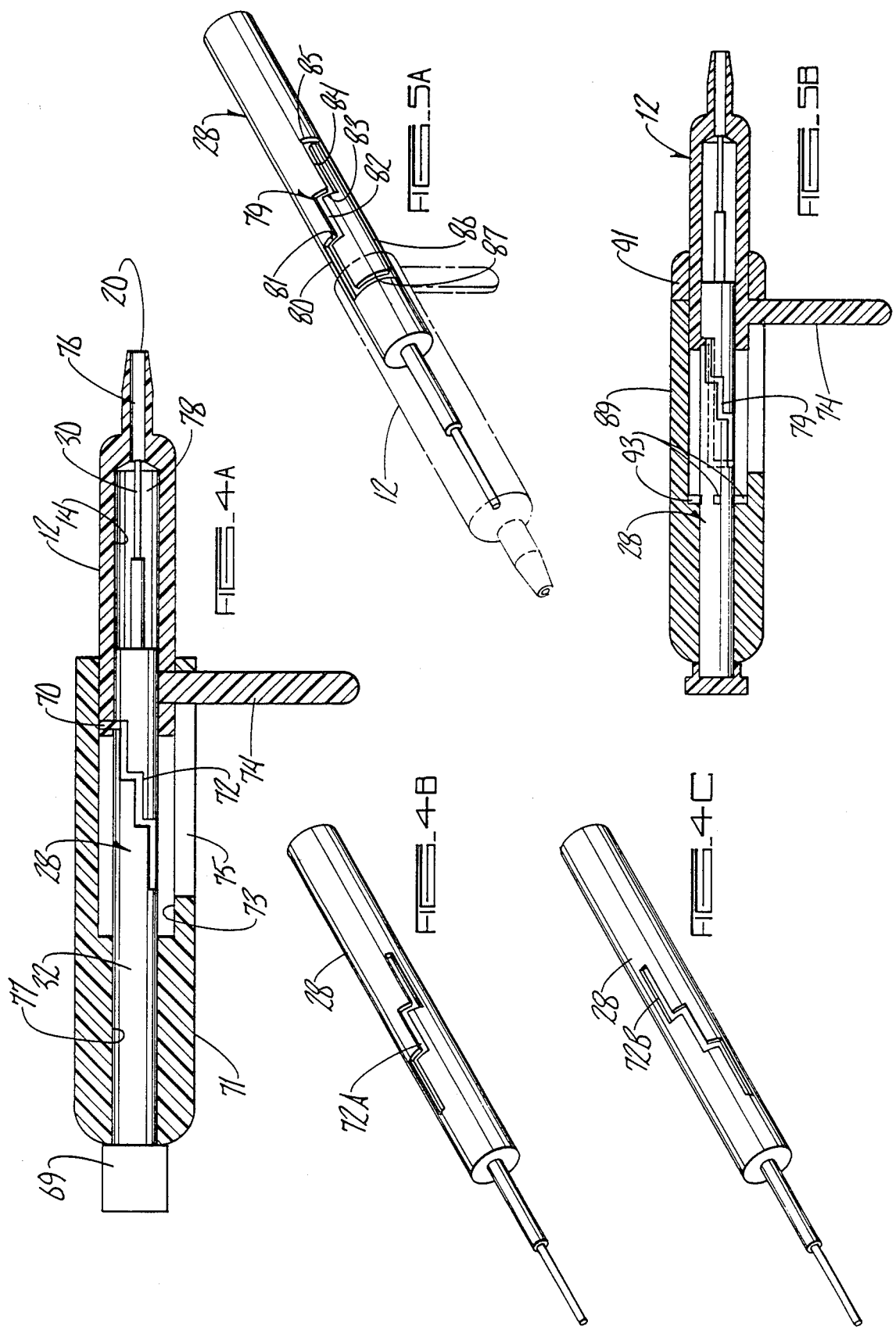

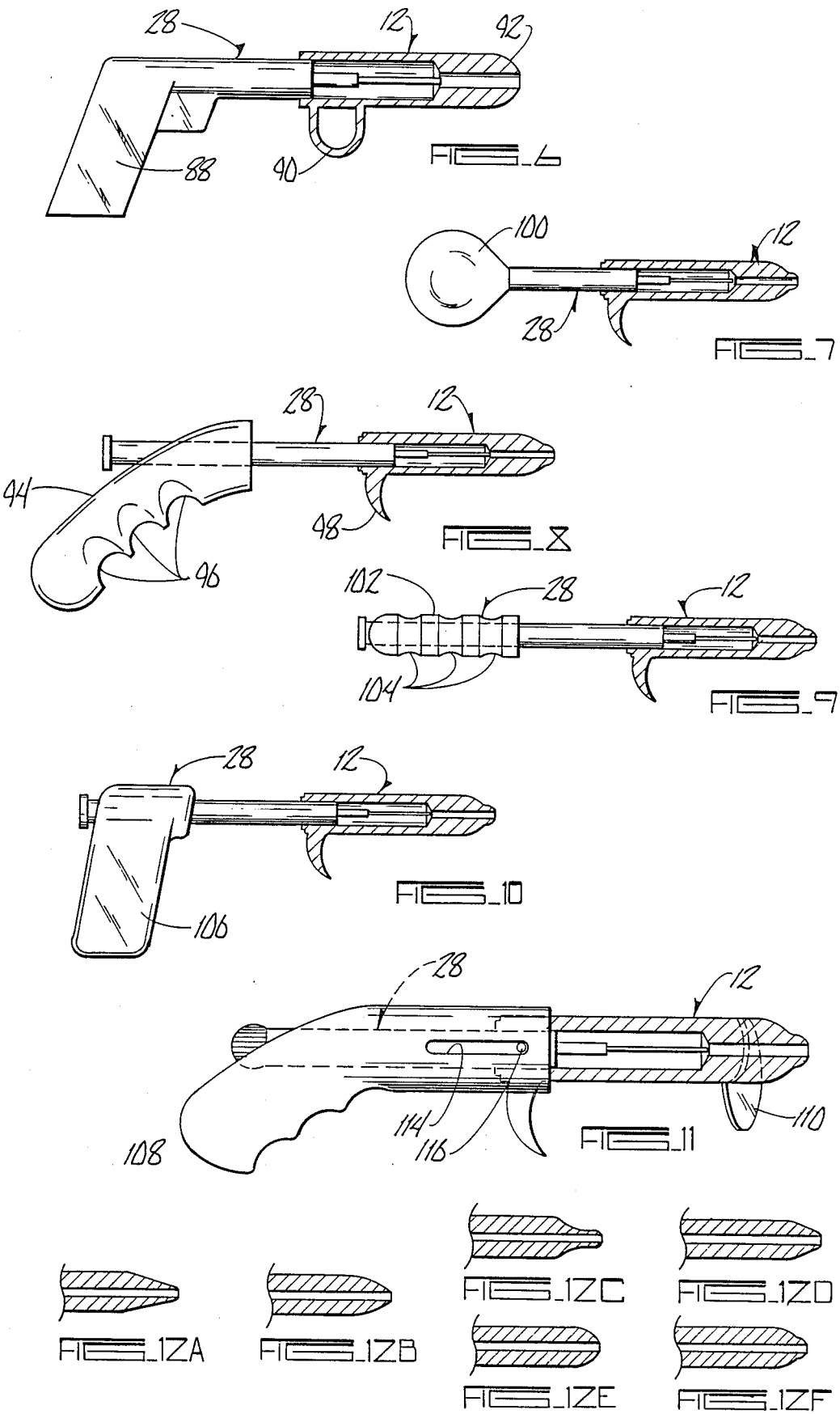

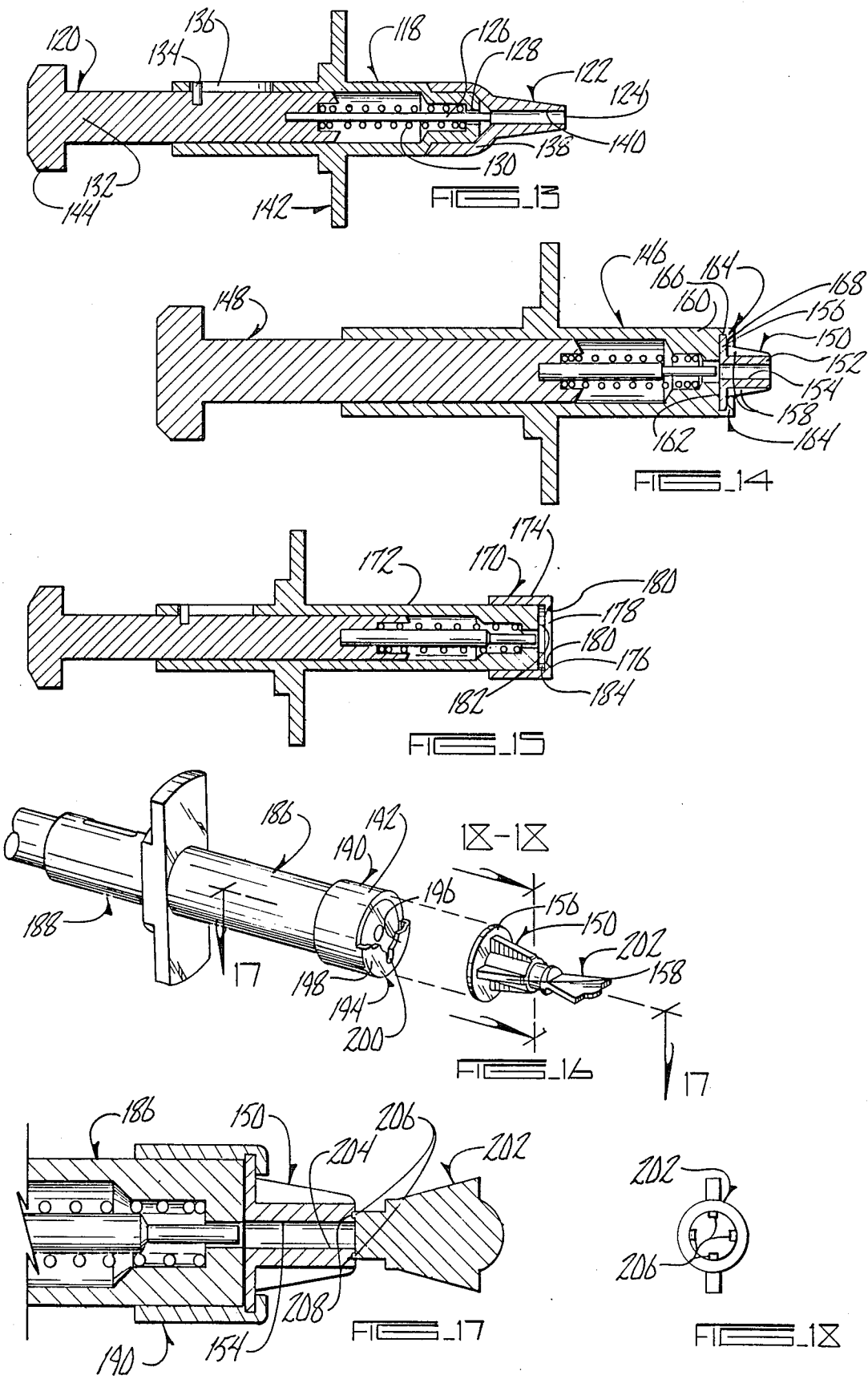

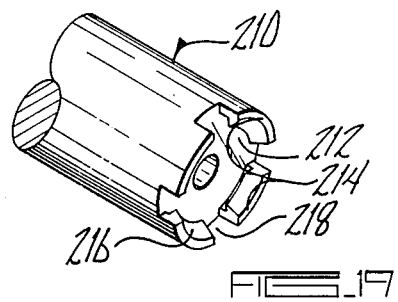
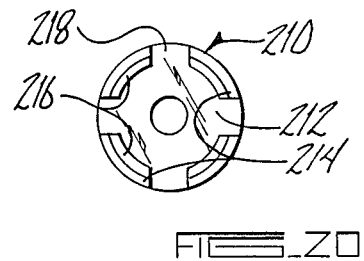
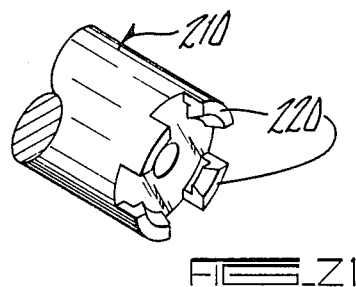
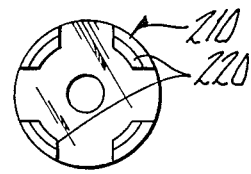
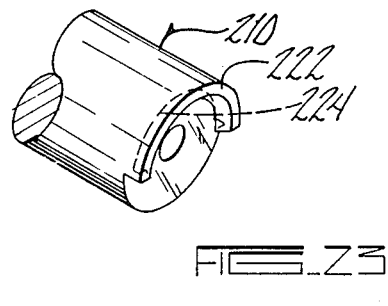
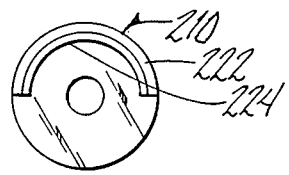

MEANS AND METHOD FOR DISPENSING SUBSTANCES

This is a continuation-in-part of co-pending application Ser. No. 948,207, filed Dec. 31, 1986 now abandoned.

BACKGROUND OF THE INVENTION

1. Field of Invention

This invention relates to a means for dispensing substances including solids, liquids, semi-solids and gels, and in particular, relates to a means which can dispense the substances precisely with easy and accurate maneuverability.

2. Problems in the Art

There are many instances where the dispensing of solids, liquids, semi-solids, or gels is required to be precise in quantity and placement. Examples are solvent, lubricant, and similar applications in, the chemical and mechanical fields, and dispensing of medication, cleansing agents, and other substances in medical, dental and veterinary fields.

Conventionally, application and dispensement occurs by ejecting the substance from its bulk, unmeasured container and approximating quantity or dosage. The container is either attempted to be positioned accurately, or the substance is first dispensed and then manually applied to the desired location. The problems with accuracy in quantity and placement are evident. In particularly sensitive or precise applications, such methods are unsatisfactory.

A real need therefore exists for a device to overcome these problems. An example of particular need exists in application or dispensing of substances and medications with regard to the human eye. Conventional methods are deficient in dose accuracy, and are not aseptic. Many times, the patient is required to apply the medication to their fingers and then attempt to apply it to their eye. Similar problems exist, however, in the other areas or fields of use discussed above.

It is therefore a primary object of the present invention to present a dispensing means for substances which solves or improves over the problems and deficiencies in the art.

A further object of the present invention is to provide a dispensing means for substances which allows precise dispensing of a quantity of the substance and precise maneuverability and placement of the substance.

A further object of the present invention is to provide a dispensing means for substances which is easily operable, and accurate.

Another object of the present invention is to provide a dispensing means for substances which can be used for a variety of substances including solids, liquids, semi-solids, and gels.

A further object of the invention is to provide a dispensing means for substances which can automatically determine dosage sizes and can dispense multiple doses.

A further object of the present invention is to provide dispensing means for substances which can be used with capillary-type containers of substances.

Another object of the present invention is to provide dispensing means for substances where the precise dosage or dosages of the substances can be pre-loaded into a removable dispensing tip, which can be disposed of after use.

These and other objects, features, and advantages of the invention will become more apparent with reference to the accompanying specification and claims.

SUMMARY OF THE INVENTION

The present invention utilizes a forward member and a rearward member, each being translateably movable with respect to each other along an axis, to form a dispensing means for substances including solids, liquids, semi-solids, and gels. The forward member includes a bore extending between its front and back ends. The front end includes an application orifice where the substances are expelled.

The rearward member includes a plunger means which is translateably moveable through the back end of the forward member into the bore. By moving the forward member with respect to the rearward member, each towards the other, the plunger moves towards the forward end of the bore and expels the substance which has been placed in the bore out of the application orifice.

In one embodiment, the forwardmost portion of the bore is narrow. The substance can be loaded into that narrow portion of the bore, and the plunger, of appropriate size, can expel the substance therefrom. In another embodiment, the substance is pre-packaged in a capillary-type container. The capillary-type container is then inserted into the bore. The plunger, having a first narrow portion, is moveable through the interior of the capillary-type container to expel the substance. A second following portion of the plunger would have an increased diameter from the first part of the plunger and would expel the capillary-type container out of the application orifice after the substance has been dispensed.

In another embodiment, a guide means can be operatively connected between the forward and rearward members to control their movement. The guide means can allow restricted axial movement between the forward and rearward members for a certain distance to control a measured expulsion of substance. The guide means can also facilitate such measured control for a plurality of doses of substance.

In a further embodiment, a dosage or dosages of a substance can be pre-loaded into a removable dispensing tip which is easily mounted on the forward member. By moving the rearward member towards the forward member, the plunger of the rearward member will expel the desired dosage. The tip is then easily removable and disposable after use.

BRIEF DESCRIPTION OF THE DRAWINGS

FIGS. 1a and 1b are sectional views of one embodiment of the invention showing the substance to be dispensed as prepackaged in a capillary-type container having two doses of substance.

FIGS. 2a and 2b are plan views of an alternative embodiment of the device of FIGS. 1a and 1b, showing a guide means which allows dispensing of two doses of a substance.

FIG. 3 is a plan view of an alternative embodiment of the device of FIGS. 1a, 1b, 2a and 2b showing a guide means with multiple dosage capability and a means to eject the capillary-type container.

FIGS. 4a–4c show other alternative embodiments of the invention.

FIGS. 5a–5b show an alternative embodiment similar to that of FIG. 4.

FIGS. 6-10 show elevational and partial sectional views of a variety of alternative embodiments for the forward and rearward sections to the invention.

FIG. 11 shows a still further alternative embodiment of the forward and rearward members of the invention with an optional guard member adjacent the application orifice and an optional retention guide means to retain and guide the forward and rearward sections with respect to each other.

FIGS. 12a-f show a variety of alternative embodiments for the front end and application orifice for the forward member of the invention.

FIG. 13 shows in cross-section an alternative embodiment of the invention including a disposable tip.

FIG. 14 shows in cross-section another embodiment of the invention, and depicts a different type of disposable tip.

FIG. 15 shows in cross-section a still further embodiment according to the invention with an alternative means for receiving the disposable tip of FIG. 14.

FIG. 16 shows in perspective view an alternative embodiment for a disposable tip receiving means of the device, and also shows in perspective a disposable tip with a break-off seal.

FIG. 17 is a cross-sectional view taken along lines 17—17 of FIG. 16.

FIG. 18 is a sectional view taken along lines 18—18 of FIG. 16.

FIG. 19 is a partial perspective view of one embodiment for a tip receiving end of the device.

FIG. 20 is an end plan view of FIG. 19.

FIG. 21 is a partial perspective view of a different disposable tip end for the device.

FIG. 22 is an end plan view of FIG. 21.

FIG. 23 is another embodiment of a disposable tip receiving end for the device.

FIG. 24 is an end plan view of FIG. 23.

DETAILED DESCRIPTION OF THE PREFERRED EMBODIMENT

The invention will now be described with respect to the drawings. The drawings represent a number of alternative embodiments of the invention as will be pointed out below.

With reference particularly to FIGS. 1a and 1b, the basic features and operation of the invention will be described. These basic features and operations apply also to the other alternative embodiments which will be described, except where otherwise pointed out.

In FIG. 1 there is shown a substance dispensing device 10 according to the invention. A forward member 12 is a generally tubular structure having a bore 14 extending between front end 16 and back end 18. An application orifice 20 is constructed at front end 16 whereas opening 22 exists at back end 18. Additionally, an opening 24 extends axially along the side of forward member 12. Opening 24 allows communication with bore 14. A washer 26 is also attached behind opening 24 towards back end 18 and serves as a finger grip for forward member 12.

A rearward member 28 is slidably insertable into bore 14 through opening 22. A forward first section 30 of rearward member 28 is of a narrower cross sectional diameter than rear section 32. Rear section 32 is of only a slightly smaller cross sectional diameter than the interior diameter of bore 14 at back end 18. This allows rearward member 28 to be firmly guided along bore 14 when rearward member 28 is moved with respect to forward member 12.

The narrower cross-sectional diameter of first section 30 allows it to push any substance which is loaded into front end 16 of forward member 12 out of application orifice 20. It is to be understood that first section 30 can be of varying diameters according to the diameter of bore 14 and application orifice 20.

In the embodiment shown in FIGS. 1a and 1b, substance 34 is pre-packaged in a capillary-type container 36 which generally consists of a tubular element having a hollow interior 38 and open ends 40 and 42. Substance 34 is generally held in container 36 by capillary action of substance 34 with respect to the interior walls of container 36. Container 36 can then be loaded into forward member 12 by passing it through opening 24 and pushing it slightly forward until it is lodged in the slightly narrowing constrictions at front end 16 and application orifice 20. A positioning means 44 in the interior of forward member 12 can cradle and insure that container 36 is positioned accurately in a generally central axial position in alignment with first section 30 of rearward member 28.

It is to be understood that FIGS. 1a and 1b container 36 holds two doses 34a and 34b of substance 34. Doses 34a and 34b are separated from one another by separation means which in this instance is simply air 46. This insures that an accurate measured dose is dispensed and provides positive assured separation between doses.

As might be shown more clearly at FIG. 1b, substance 34 is dispensed by moving forward member 12 and rearward member 28 towards each other so that first section 30 of rearward member 28 moves towards and into hollow interior 38 of container 36. It is to be understood that container 36 is aligned to receive first section 30 and the cross-sectional diameter of first section 30 is slightly less than the inside diameter of hollow interior 38. Container 36 thus stays intact in bore 14. Continued movement of rearward member 28 thus pushes substance 34b forwardly, which in turn pushes air 46 and substance 34a. Substance 34a is then precisely and controllably expelled from application orifice 20. Continued movement of rearward member 28 would move substance 34b in position to likewise be dispensed.

By retracting or moving rearward member 28 away from forward member 12, first section 30 can be withdrawn in back of opening 24 and allow a reloading of a new container 36. The old dispensed container 36 can be easily grabbed and removed prior to insertion of a new container 36.

It can therefore be seen that the present invention achieves its objectives in allowing a user to easily and precisely dispense many types of substances.

FIGS. 2a and 2b show a further feature and embodiment of the invention generally shown at FIGS. 1a and 1b. To more accurately control movement of rearward member 28 with respect to forward member 12, a guide means can be incorporated into members 12 and 28. A pin 48 can be secured extending outwardly and perpendicularly from the longitudinal axis of rear section 32 of rearward member 28. A slot 50 can be formed through the wall or on the surface of forward member 12. When rearward member 28 is inserted into back end 18 of forward member 12, pin 48 can be introduced into slot 50. Slot 50 has a first linear section 52 which is parallel to the axis of dispensing device 10. The user would grasp washer 26 and pull forward member 12 over rearward member 28. Pin 48 in slot 50 would control this movement by allowing this travel to continue only until pin 48 comes against stop 54 at the forward end of linear section 52. By coordinating the length of linear section 52 with the length of first section 30 of rearward member 28, a measured dosage of substance can be dispensed from application orifice 20. Thus, in relation to FIGS. 1a and 1b, front substance 34a would be dispensed, and nothing more. FIGS. 2a and 2b also show that slot 50 can be continued by perpendicular section 56 and second linear section 58. Rearward section 28 needs only to be backed up from stop 54, end knob or dial 60 turned clockwise, and then again brought forward to dispense second substance 34b. Second stop 62 would then stop all forward movement of rearward member 28. By following a reverse procedure, rearward member 28 can be moved back and the device reloaded.

FIGS. 2a and 2b also show an alternative front end 63 for forward member 12. Front end 63 has a narrowing forward portion terminating in application orifice 20. Additionally, loading of capillary-type containers 36 into forward member 12 is accomplished by decreasing the diameter of bore 14 to a narrowed portion 65 which extends through front end 63. An intermediate narrow portion 67 bridges the change in diameter between bore 14 and narrowed portion 65. Capillary-type container 36 can thus be inserted through opening 24 and be positioned and held centrally and axially within narrowed portion 65 in alignment with front section 30 of rearward member 28.

FIG. 3 shows still a further alternative feature of the invention. The pin and slot arrangement functions similarly to that of FIGS. 2a and 2b. However, in this embodiment, slot 64 has a third linear section 66 which extends all the way to washer 26. Additionally, rearward member 28 includes a second section 68 between first section 30 and rear section 32. Section 68 is of slightly larger cross-sectional diameter than first section 30, but of narrower cross-sectional diameter than rear section 32. By referring to capillary-type container 36 in FIGS. 1a and 1b, it is to be understood that section 68 cooperates with third linear section 66 so that once first section 30 has passed through hollow interior 38 of capillary-type container 36 and expelled all doses of substance 34, the larger cross-sectional diameter of section 68, being greater than the inside diameter of hollow interior 38, would abut the rearward end of container 36 and cause container 36 to be expelled out of application orifice 20.

It is to be understood that the distances, lengths, and position of the various relevant elements can be selected and constructed in a manner to allow the device to operate as above described. Selection of these parameters, is well within the skill of those with ordinary skill in the art.

FIGS. 4a-c show alternative embodiments of the invention utilizing a similar guide means to that previously described. However, in this embodiment, pin 70 is secured in forward member 12 and extends down into bore 14, whereas slot 72 is constructed in second section 32 of rearward member 28. FIG. 4a shows that a trigger 74 could be substituted for a washer 26 and be used as a grip to pull forward member 12 back over rearward member 28. It can also be seen that bore 14 requires a narrow portion 76 near application orifice 20 and a wider portion 78 to facilitate the functioning of downward extending pin 70.

In the embodiment of FIG. 4, pin 70 and slot 72 again cooperate to allow dispensement of two doses from application orifice 20 by virtue of first section 30 of rearward member 28, and then expels any remaining substance 34 and/or capillary-type container 36 in cooperation with second section 68 of rearward member 28. Dial or knob 69 is turned to allow continued axial movement of forward and rearward members 12 and 28 with respect to one another.

FIG. 4a also shows the use of an overlay handle 71 which basically surrounds and contains most of rearward member 28. Overlay handle 71 is open at both ends and has a first bore 73 which contains the rearward end of forward member 12 and a substantial portion of rearward member 28. Slot 75 communicates with first bore 73 and serves as a guide for trigger 74 which is attached to forward member 12. A second bore 77 follows first bore 73 and closely conforms to the diameter of rear section 32 of rearward member 28. It is to be understood that overlay handle 71 allows rearward member 28 to rotate within it so that dial or knob 69 can be used to facilitate operation of pin 70 and slot 72, but overlay handle 71 joins forward and rearward member 12 and 28 and facilitates their better movement between one another. It also provides a better gripping portion for the rear part of the device. It is to be understood that in this embodiment, substance 34 and/or capillary-type container 36 can simply be inserted into narrow portion 76 through application orifice 20 to load the device.

FIG. 4b and 4c simply show that slot 72 of FIG. 4a can assume different configurations and still function as required for the invention. For example, FIGS. 4b and 4c show the three-step slots 72a and 72b, which are simply oppositely configured from each other.

FIG. 5a and 5b show a different slot arrangement 79 which can be used similarly to the pin and slot guide means previously described. Slot 79 allows an easier returning of the pin back to a starting or reloading position by providing a complete circuit path. The circuit path of slot 79 is comprised of first linear portion 80, perpendicular step 81, second linear portion 82, step portion 83, and third linear portion 84. This is essentially the same as shown in Figure 4a. Additionally, another step portion 85 connects into a return section comprised of portions 86 and 87. Instead of having to reverse the travel of the pin through the linear portions and steps, when the pin reaches the rearward end of linear portion 84, rearward member 28 needs only to be rotated slightly through step 85 and then pulled backwardly through portion 86, and then turned back again through portion 87 to return to a starting/loading position.

FIG. 5b shows the forward and rearward sections 12 and 28 of FIG. 5a with slot 79. Additionally, an overlay handle 89, similar to overlay handle 71 of FIG. 4a, is incorporated therein. It is noted that overlay handle 89 differs in that an end cap 91 comprises the front portion of overlay handle 89. This allows trigger 74 to be one piece with forward section 12. By removing end cap 91, forward section 12 can be separated from rearward section 28. It is also noted that rearward section 28 has a plurality of stop pins 93 extending perpendicularly from its longitudinal axis behind slot 79. Stop pins 93 prohibit movement of rearward member 28 rearwardly.

FIGS. 6-10 show alternative embodiments for construction of the forward member 12 and rearward member 28. FIG. 6 shows a gun handle 88 with a loop trigger 90 in forward member 92. FIG. 8 shows a modified pistol grip 94 with finger holds 96 for easier gripping action. Trigger 98 is shown in modified form.

FIG. 7 shows a bulb handle 100 for an alternative gripping method, whereas FIG. 9 shows a straight handle grip 102 with finger holds 104. FIG. 10 shows a modified gun handle 106.

It is to be understood that all of these embodiments function similarly to what has been previously described, and can include pin sand slot guide means for multiple dosage and container ejection, and other applicable features. These embodiments shows different alternative features which may be advantageous for different applications.

FIG. 11 shows an embodiment having a modified pistol grip 108. In this embodiment, however, forward member 12 slidably fits within pistol grip 108. By incorporating suitable means such as pins, flanges, or stop members, this embodiment can be kept in basically one piece so that forward and rearward members 12 and 28 cannot be separated apart. In the embodiment of FIG. 11, there is shown an optional arrangement whereby slots 114 exist on opposite sides of pistol grip 108. Pins 116 extend from forward member 12 through slots 114 to act as guides and retaining means. It is understood that rearward member 28 is rotatable within pistol grip 108. FIG. 11 also shows an optional guard 110 which is particularly valuable in applications of medications to the eye to restrain any errant medication from contacting nondesired areas of the eye or face.

FIGS. 12a-f simply show alternative embodiments for front end 16 of forward member 12 and for application orifices 20. These alternative designs have advantageous applications in different uses.

The present invention can also utilize the general means and method described above regarding a forward member which slidably receives a rearward member. When these two members are brought towards one another, the plunger on the rearward member expels a substance out of an application orifice in the tip of the forward member. In these alternative embodiments, however, a disposable tip which can be pre-loaded with the substance, is removably positioned on the end of the forward member. This arrangement allows for easier use, disposability of the tip, and reduces manufacturing costs. Embodiments utilizing a disposable tip will now be described.

FIG. 13 depicts one embodiment of the device according to the invention with a disposable tip. Forward member 118 and rearward member 120 operate generally the same as the previously described embodiments. In this embodiment, however, a disposable tip 122 which includes an application orifice 124 is fittable to the front of forward member 118. The narrowed first section 126 of rearward member 120 movably extends through aperture 128 in the front of forward member 118.

A spring 130 surrounds first section 126 and extends between the interior side of the front of forward member 118 back to the rear section 132 of rearward member 120. Pin 134, secured in rearward member 120, moves within slot 136 of forward member 118 and determines the limits of movement of these two members with respect to one another. Spring 130 always returns the device to a loading position after substances are dispensed. Disposable tip 122 can optionally be pre-loaded with a substance and can contain a break-off or removable seal over application orifice 124.

In the embodiment of FIG. 13, enlarged end 138 of disposable tip 122 fits over the front of forward member 118. It is to be understood that disposable tip 122 can be made of a somewhat resilient material so that enlarged end 138 frictionally fits over the front end of the forward member 118. Other methods, such as are well within skill in the art, can be used to accomplish detachable retentive engagement of disposable tip 122 to the forward member 118.

It is further to be understood that the arrangement shown in FIG. 13 allows a disposable tip to be preloaded with a substance to be dispelled. The substance would be pre-loaded into bore 140 in disposable tip 122, or alternatively, could be contained in some sort of a capillary container. Disposable tip 122 could be sealed or otherwise covered until it is positioned on forward member 118. Disposable tip 122 thus allows easy and efficient preparation of a dosage of the substance for use.

A user would position the device of FIG. 13 so that the user's fingers would abut the forward surfaces of flange 142 and the user's palm would abut rear end 144 of rearward member 120. By pulling the user's fingers towards the palm, rearward member 120 would slidably move within forward member 118 causing plunger or narrowed first section 126 of rearward member 120 to dispel the substance within bore 140 out of application orifice 124. Additionally, it is to be understood that this type of movement would draw the application orifice 124 away from the location where the substance is being dispelled. This is particularly important in applications such as dispensing of medications to a person's eyes, where contact with the tip is to be avoided, and even represents a significant danger. Pin 134 in slot 136 would stop the forward movement of narrowed first section 126, to also prevent any damage or injury caused by first narrowed section 126 extending out of application orifice 124.

After dispensing of the substance, the user's fingers would be relaxed and spring 130 would bias and move forward member 118 back to the position shown in FIG. 13. Disposable tip 122 can be easily detached and disposed of, and the device is ready for reuse.

FIG. 14 depicts an alternative embodiment of the dispensing device according to the invention. Operation of the forward member 146 and rearward member 148 is essentially the same as forward and rearward members 118 and 120 of FIG. 13. In the embodiment of FIG. 14, no pin 134 or slot 136 is shown, but it is to be understood that they also could be incorporated into this embodiment.

In FIG. 14, disposable tip 150 comprises a tubular section 152 having a center bore 154 which can be preloaded with a substance to be dispensed. An annular flange 156 surrounds the rearward end of tubular section 152. Raised angled ribs 158 also are positioned in spaced apart locations around the perimeter of tubular section 152, and serve to support annular flange 156.

The forward end 160 of forward member 146 contains a generally cylindrical recess 162 which receives annular flange 156 of disposable tip 150. Projections 164 are positioned around the perimeter of cylindrical recess 162, and have first sections 166 extending parallel to the longitudinal axis of forward member 148, and have second sections 168 which extend radially inward with respect to cylindrical recess 162.

Projections 164, or annular flange 156, can be made of a pliant, yet resilient material, so that annular flange 156 can "snap in" to cylindrical recess 162, and be held there to allow dispensing of the substance. This property then allows disposable tip 150 to be easily removed from cylindrical recess 162 and disposed of.

FIG. 15 shows a still further alternative embodiment of the dispensing device according to the present invention, utilizing disposable tips 150, as shown in FIG. 14. In the embodiment of FIG. 15, a cap 170 is secured by means known within the art to the forward end of forward member 172. Cap 170 comprises a tubular section 174 which surrounds the forward end of forward member 172. A front wall 176 is formed at the front end of tubular section 174. Front wall 176 includes an aperture 178 being defined by angled side edges in front wall 176. Front wall 176 is spaced apart from front edge 182 of forward member 172.

Thus, as in FIG. 14, the annular flange 156 of a disposable tip 150 could be snapped-in through aperture 178 to the space 184 between front wall 176 of cap 170, and the front edge 182 of forward member 172. Dispensing of the substance from disposable tip 150 would be accomplished in the same manner as described with regard to FIGS. 13 and 14.

FIG. 16 shows in perspective a forward member 186 and rearward member 188 which function the same as forward and rearward members described with respect to FIGS. 13, 14, and 15. A cap 190 is secured to the forward end of forward member 186, and detachably receives disposable tip 150. In this embodiment, cap 190 includes a tubular section 192, and a cradle 194 extending outwardly from tubular section 192. Cradle 194 essentially consists of a semi-circular wall 196 extending from tubular section 192. A front wall 198 extends from the front edge of semi-circular wall 196. A slot 200 is formed in front wall 198.

Annular flange 156 of disposable tip 150 is thus slid perpendicularly to the longitudinal axis of forward member 186 into the interior or "cradle" formed by semicircular wall 196 and front wall 198, with respect to the front of forward member 186. The raised angled ribs 158 of disposable tip 150 are positioned so that one of the raised angled ribs 158 is received into slot 200. Disposable tip 150 would thus be retained sufficiently to allow dispensing of the substance.

An additional feature is shown in FIG. 16. Disposable tip 150 can have a snap-off seal 202 covering its application orifice 204 (see FIG. 17), to facilitate loading of a substance into disposable tip 150. The configuration of cap 190 and cradle 194 in FIG. 16 thus not only retains the disposable tip 150 for dispensing of the substance, but also slot 200 cooperates with raised angled rib 158 to prevent rotation of disposable tip 150 within cradle 194 when seal 202 is twisted to break it off from disposable tip 150.

By referring to FIGS. 17 and 18, the exact configuration of seal 202, and its orientation to disposable tip 150 can be seen. By manufacturing processes known to those skilled in the art, seal 202 can be secured to the front end of disposable tip 150. One way to accomplish this is to have small feet 206 extend from seal 202 into small notches 208 in disposable tip 150. Feet 206 can thus be welded or otherwise adhered to notches 208 in such a manner that rotational force of seal 202 would cause it to break off from disposable tip 150 cleanly with minimal manual effort. The bond should be strong enough, however, to withstand normal shipment forces.

It is also to be understood that the rear of disposable tip 150 (across flange 156) could also be sealed by means well known within the art. For example, a sheet of material could be adhered over annular flange 156 to block the rear end of bore 154. The sheet of material could be such that it would be easily punctured by the plunger or first narrowed section of rearward member of the dispensing device when the disposable tip is held in position or it could be removed prior to mounting of the disposable tip.

FIGS. 19–24 depict alternative embodiments for means by which disposable tips can be detachably retained in the end of a forward member 210. FIGS. 19 and 20 depict retaining means similar to that shown in FIG. 14 where a cylindrical recess 212 is bounded by inwardly directed portions 216. A round annular flange of a disposable tip such as that shown in FIGS. 14, 16, 17, would snap into cylindrical recess 212 and be held by portions 216 of projections 214 until the substance is dispensed. Gaps 218 between projections 214 would receive the raised angled ribs of the disposable tip such as 150 in FIG. 14, and prevent rotation of tip 150.

FIGS. 21 and 22 are essentially the same as FIGS. 19 and 20, but show that the width of projections 220 can be varied. In FIGS. 21 and 22, projections 220 are narrower to accommodate wider raised angled ribs of disposable tip 150, or otherwise allow easier insertion and removal of the disposable tip.

Finally, FIGS. 23 and 24 show a semi-circular cradle 222 similar to that shown in FIG. 16. Cradle 222, however, has a lip 224 which serves to retain annular flange 156 of disposable tip 150. This arrangement may allow for easier insertion and removal of disposable tip 150 to the dispensing device.

It can therefore be seen that the embodiments of FIGS. 13–24 allow the ease of a disposable tip having a premeasured, pre-loaded dosage of the substance to be easily dispensed. The dispensing device allows the substance to be precisely directed to the desired location, and eliminates any contact of the substance with the user's hands. This maintains a sterile and non-contaminated method of dispensing the substance.

Substances to be dispensed can be solid, semi-solid, or even liquid.

The disposable tips can be made of material such as polypropylene to allow them to have some pliancy and resiliency. Of course, other materials are equally suitable.

Different sized disposable tips can be utilized. It is to be understood that tips with long interior bores could contain multiple pre-loaded dosages of a substance. The disposable tips of FIGS. 13–24 could therefore also be used with the previously described embodiments having pins which are movable through stepped slots to give exact predetermined dispensing of dosages.

It will be appreciated that the present invention can take many forms and embodiments. The true essence and spirit of this invention are defined in the appended claims, and it is not intended that the embodiment of the invention presented herein should limit the scope thereof.

What is claimed is:

1. A dispensing means for substances including solids, liquids, semi-solids, and gels, comprising:
    a forward member having a bore extending between front and back opposite ends, said bore terminating in an application orifice at said front end;
    a rearward member being translateably movable with respect to said forward member and having a plunger means which extends through said back and is slibably movable within said bore of said forward member;

said substance being positionable in said bore between said front and back ends so that movement of said rearward member with respect to said forward member causes said plunger to expel said substance from said application orifice; and said substance being contained within a capillary-type container which is positionable within said bore, said capillary-type container comprising a tubular means having first and second open ends, said substance being normally held by capillary action within the interior hollow of said tubular means.

2. The means of claim 1 wherein said capillary-type container can hold one or more doses of substance, said doses being separated by a separation means.

3. The means of claim 1 wherein said container is insertable into a narrow portion of said bore, said narrow portion extending rearwardly from said application orifice.

4. The means of claim 1 further comprising a guide means operatively engageable between said forward and rearward members for controlling direction and amount of movement between said forward and rearward members.

5. A dispensing means for accurate, uniform, and reliable unit dose dispensing of ophthalmic substances including solids, liquids, and semi-solids, comprising:

a forward member having a bore extending between front and back opposite ends;

a disposable, replaceable, removable unit dose tip means having a bore extending therethrough for containing a pre-loaded unit dose substance, the unit dose tip means including a proximal end and an outwardly extending non-enclosed distal end with the unit dose being held therebetween;

securing means for mounting the proximal end of the tip means to the front end of the forward member, the tip means extending to said non-enclosed distal end for application of the unit dose to a user's eye, the tip means then being disposable; and a rearward member including a plunger means having a forward end which is translateably movable within the bore of the forward member and within the bore of the tip means to dispel the pre-loaded substance upon movement of the forward member with respect to the rearward member when the tip means is secured to the forward member, but without extending out of the distal end of the tip means.

6. The means of claim 5 wherein the securing means comprises:

an outer receiving surface at the front end of the forward member;

a gripping portion at one end of the tip means, the gripping portion including a gripping surface which contacts and releasably secures the tip means to the receiving surface of the forward member.

7. The means of claim 6 wherein the gripping portion comprises one end of the bore of the tip means, and the gripping surface comprises the interior walls of the tip means defining the bore of the tip means.

8. The means of claim 7 wherein the gripping portion of the tip means is resiliently biased to the receiving surface of the forward member to secure the tip means to the forward member.

9. The means of claim 5 wherein the securing means comprises an enlarged and resilient end of the tip means including an enlarged portion of the bore of the tip means having an inside dimension less than the outside dimension of the front end of the forward section.

10. The dispensing means of claim 5 wherein the securing means comprises:

an annular flange means on the tip means;

receiving means positioned at the front end of the forward member for releaseably securing at least a portion of the annular flange means to the forward member.

11. The dispensing means of claim 10 wherein the receiving means comprises a recess in the front end of the forward member of slightly larger inside diameter than the outside diameter of the annular flange means, and includes retaining means to releaseably secure the annular flange to the recess.

12. The dispensing means of claim 11 further comprising stop means for preventing rotation of the tip means relative to the bore of the tip means when secured to the forward section.

13. The dispensing means of claim 12 wherein the stop means comprises a slot in the retaining means which receives a raised portion of the tip means.

14. The dispensing means of claim 10 wherein the receiving means comprises a cap means securable over the front end of the forward member, the cap means including an aperture defined by the retaining members through which the annular flange of the tip means is releasably insertable and securable.

15. The dispensing means of claim 14 wherein the retaining members define an aperture that is smaller in diameter than the outside diameter of the annular flange of the tip means.

16. The dispensing means of claim 10 wherein the securing means comprises a cap means including an extended portion, a slot in the extended portion perpendicular to the bore to receive a portion of the annular flange.

17. The dispensing means of claim 16 wherein the portion of the annular flange received in the slot is a raised portion of the tip means and holds the tip means from rotation with respect to the receiving means.

18. A means for accurate and safe single unit dosage dispensing of ophthalmic substances including solids, liquids, and semi-solids, and gels comprising:

a disposable replaceable tip means having a capillary-type bore extending therethrough pre-loaded with the single unit dosage of the substance, the tip means including a proximal end and an outwardly extending non-enclosed distal end with the unit dosage of the substance being held in the capillary-type bore of the tip means;

an annular flange at the proximal end of the tip means surrounding and extending generally radially outwardly from the capillary-type bore of the tip means, the tip means extending to said non-enclosed distal end for application of the unit dose to a user's eye, the tip means then being dispensable; and a dispenser body means having a front end including a receiving means for releasably securing the annular flange of the tip means.

19. A method for accurate and safe single unit dosage dispensing of ophthalmic medications and substances including solids, liquids, semi-solids, and gels comprising:

pre-loading a pre-measured single unit dosage of substance in a disposable tip having a capillary-type bore therethrough, the tip having a proximal end and an non-enclosed distal end;

detachably securing the proximal end of the disposable tip to a dispensing means having a forward member which includes a bore therethrough, and a rearward member having a plunger which is slidably movable within the bore of the forward member, the tip extending to said non-enclosed distal end;

using the distal end of the tip to dispense the single unit dosage to a user's eye;

moving the forward member with respect to the rearward member so that the plunger moves through the bore of the forward member and the bore of the tip means to dispel the substance from the bore of the tip means;

precluding the plunger from moving outside the distal end of the tip to protect the user's eye during dispensing of the single unit dosage; and removing the tip means after dispensing the single unit dosage to enable another disposable tip means to be secured to the dispensing means for another single unit dosage application of the substance.

20. A dispensing means for substances including solids, liquids, and semi-solids, comprising:

a forward member having a bore extending between front and back opposite ends;

a removable tip means having a bore extending therethrough for containing a pre-loaded substance;

securing means for mounting the tip means to the front end of the forward member, the securing means comprising an annular flange means on the tip means and receiving means positioned at the front end of the forward member for releaseably securing at least a portion of the annular flange means to the forward member, the receiving means comprising a recess in the front end of the forward member of slightly larger inside diameter than the outside diameter of the annular flange means, and including retaining means to releasably secure the annular flange to the recess;

a stop means for preventing rotation of the tip means relative to the bore of the tip means when secured to the forward section; and a rearward member including a plunger means having a forward end which is translateably movable within the bore of the forward member and within the bore of the tip means to dispel the pre-loaded substance upon movement of the forward member with respect to the rearward member, when the tip means is secured to the forward member.

21. The dispensing means of claim 20 wherein the stop means comprises a slot in the retaining means which receives a raised portion of the tip means.

* * * * *